(12) United States Patent
Lee et al.

(10) Patent No.: US 10,219,824 B2
(45) Date of Patent: *Mar. 5, 2019

(54) METHODS AND DEVICES FOR CUTTING TISSUE

(71) Applicant: Covidien LP, Mansfield, MA (US)

(72) Inventors: Kee Lee, Newark, CA (US); Phyllis Yuen, Fremont, CA (US); Darren Doud, San Jose, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 15/246,201

(22) Filed: Aug. 24, 2016

(65) Prior Publication Data

US 2016/0374718 A1 Dec. 29, 2016

Related U.S. Application Data

(63) Continuation of application No. 14/280,713, filed on May 19, 2014, now Pat. No. 9,445,834, which is a continuation of application No. 12/325,797, filed on Dec. 1, 2008, now Pat. No. 8,784,440, which is a continuation of application No. 12/283,224, filed on Sep. 9, 2008, now abandoned.

(60) Provisional application No. 61/067,238, filed on Feb. 25, 2008.

(51) Int. Cl.
*A61B 17/3207* (2006.01)

(52) U.S. Cl.
CPC ............... *A61B 17/320758* (2013.01); *A61B 17/320725* (2013.01); *A61B 17/320783* (2013.01); *A61B 17/32075* (2013.01); *A61B 2017/320791* (2013.01)

(58) Field of Classification Search
CPC ...... A61B 17/320783; A61B 17/32075; A61B 17/320758; A61B 17/32002; A61B 17/3207; A61B 2017/320791; A61B 2017/320766

See application file for complete search history.

(56) References Cited

U.S. PATENT DOCUMENTS

| 1,481,078 | A | 1/1924 | Albertson |
| 2,178,790 | A | 11/1939 | Henry |
| 2,701,559 | A | 2/1955 | Cooper |
| 2,850,007 | A | 9/1958 | Lingley |
| 3,064,651 | A | 11/1960 | Henderson |
| 3,082,805 | A | 3/1963 | Royce |
| 3,320,957 | A | 5/1967 | Sokolik |

(Continued)

FOREIGN PATENT DOCUMENTS

| CA | 2000621 | 4/1990 |
| DE | 3732236 C1 | 12/1988 |

(Continued)

OTHER PUBLICATIONS

Extended European Search Report for Application No. 13163446.1, dated Aug. 2, 2013, 4 pages.

(Continued)

*Primary Examiner* — Sarah W Aleman
(74) *Attorney, Agent, or Firm* — Stinson Leonard Street LLP

(57) ABSTRACT

A catheter is provided, which includes a cutting element having one or more raised elements. The cutting element has a cup-shaped surface at the distal end that may be smooth and continuous except for the raised elements.

8 Claims, 8 Drawing Sheets

(56) References Cited

U.S. PATENT DOCUMENTS

| | | |
|---|---|---|
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMichael et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |

(56) References Cited

U.S. PATENT DOCUMENTS

| | | |
|---|---|---|
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |

(56) References Cited

U.S. PATENT DOCUMENTS

| | | |
|---|---|---|
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |

(56) References Cited

U.S. PATENT DOCUMENTS

| | | |
|---|---|---|
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,784,440 B2 * | 7/2014 | Lee ............... A61B 17/320725 606/159 |
| 9,445,834 B2 * | 9/2016 | Lee ............... A61B 17/320725 |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0270966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |

(56) References Cited

U.S. PATENT DOCUMENTS

| | | | |
|---|---|---|---|
| 2011/0022069 A1 | 1/2011 | Mitusina | |
| 2011/0040315 A1 | 2/2011 | To et al. | |
| 2011/0130777 A1 | 6/2011 | Zhang et al. | |
| 2011/0144673 A1 | 6/2011 | Zhang et al. | |

FOREIGN PATENT DOCUMENTS

| | | | |
|---|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0983749 A2 | 3/2000 |
| EP | 1767159 A1 | 3/2007 |
| EP | 1875871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | 199316642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | 200030531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 A2 | 6/2006 |

OTHER PUBLICATIONS

Huang et al., "Optical Coherence Tomography," Science, 254: 11788-1181 (1991).
Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Chinese Office action for Application No. 200980107019.3, dated Sep. 12, 2013, 6 pages.
Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).
Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

\* cited by examiner

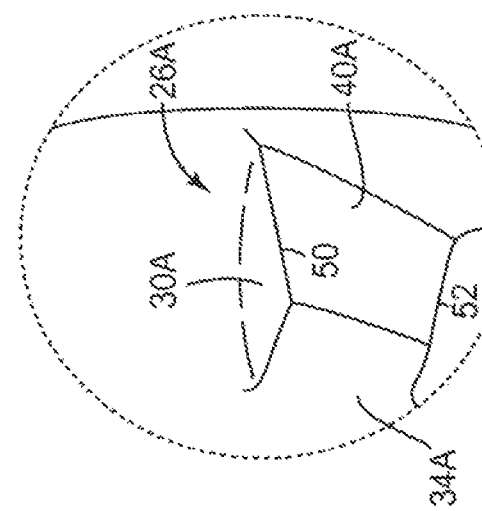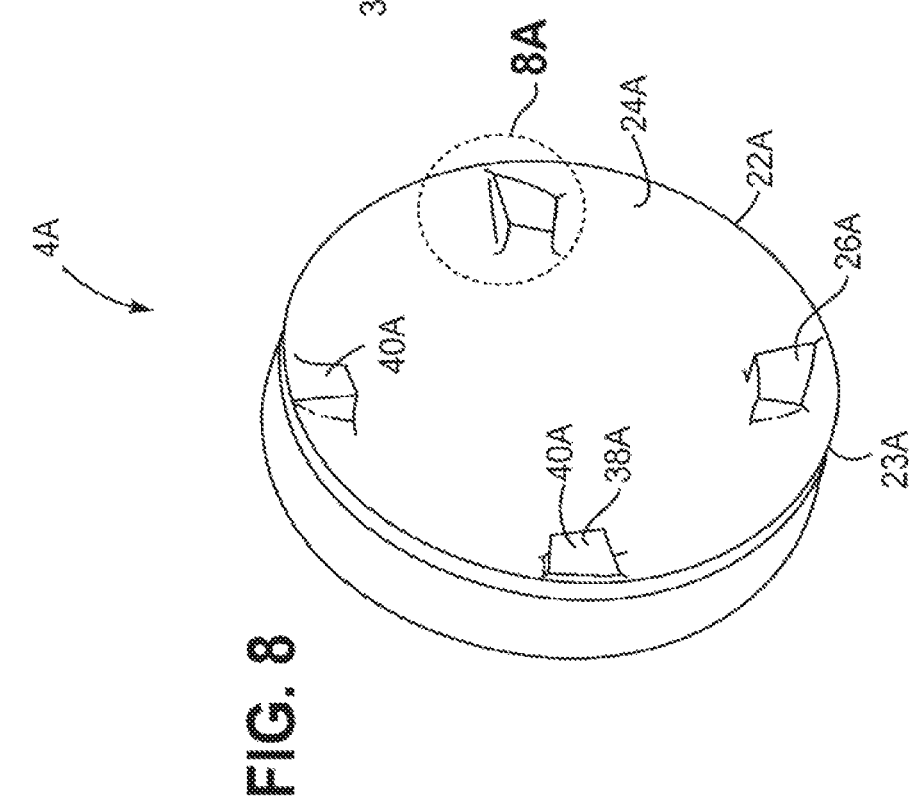
FIG. 8
FIG. 8A

METHODS AND DEVICES FOR CUTTING TISSUE

CROSS-REFERENCE TO RELATED PATENT APPLICATIONS

This application is a continuation of U.S. Ser. No. 14/280,713, filed May 19, 2014, which is a continuation of U.S. Ser. No. 12/325,797 filed Dec. 1, 2008, now U.S. Pat. No. 8,787,440, which is a continuation of U.S. Ser. No. 12/283,224 filed Sep. 9, 2008, which claims the benefit of provisional application Ser. No. 61/067,238, filed Feb. 25, 2008, the contents of each of which are hereby incorporated herein by reference.

BACKGROUND

Atherectomy catheters are used to remove material from a blood vessel to open the blood vessel and improve blood flow through the vessel.

One problem that occurs when removing material from a blood vessel is that the material may be either soft or hard and may vary during the cutting process. As such, the cutting element should be able to cut both hard tissue and soft tissue.

The present invention is directed to a cutting element for an atherectomy catheter and methods of cutting material from a blood flow lumen using a rotating cutting element.

SUMMARY

The present invention provides an atherectomy catheter, which has a cutting element that is able to cut both soft tissue and hard tissue. The cutting element has a sharp cutting edge that surrounds a cup shaped surface. The cup-shaped surface directs the material, which has been cut into a tissue chamber. The circumferential cutting edge and the cup-shaped surface together are well suited to cut and remove relatively soft tissue.

In one aspect of the invention, an atherectomy catheter is provided which has one or more raised elements extending from the cup-shaped surface. The raised element may be recessed longitudinally and radially from the outer cutting edge by a controlled distance such as 0.0010-0.0020 inch but may, of course, be closer or briber from the outer cutting edge depending upon the application. The raised elements help to break up had tissue such as calcified plaque. The raised elements are somewhat recessed from the distal end so that the cutting edge remains exposed to cut soft tissue. When the cutting element encounters tissue, which is too hard to be cut sufficiently by the cutting edge, the raised elements help to break the harder tissue with a more blunt application of force.

In another aspect of the invention, the raised element is somewhat small so that a relatively large portion of the cup-shaped surface is smooth and uninterrupted. In this manner, the ability of the cutting element to direct tissue into the tissue chamber with the cup-shaped surface is not overly inhibited by the raised elements. For example, the raised elements may occupy an area less than 60 degrees when viewed along the longitudinal axis. Stated another way, the cup-shaped surface of the cutting element is smooth and uninterrupted throughout at least 300 degrees when viewed along the longitudinal axis. Stated still another way, the cup-shaped surface may be smooth and uninterrupted for at least 95% of the surface area of the cutting element when viewed along the longitudinal axis.

These and other aspects will become apparent from the following description of the preferred embodiments, drawings and claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8 shows the embodiment of the cutting element of FIG. 7
and FIG. 8A shows one of the raised elements of the cutting element embodiment.

DETAILED DESCRIPTION

Figure 1:
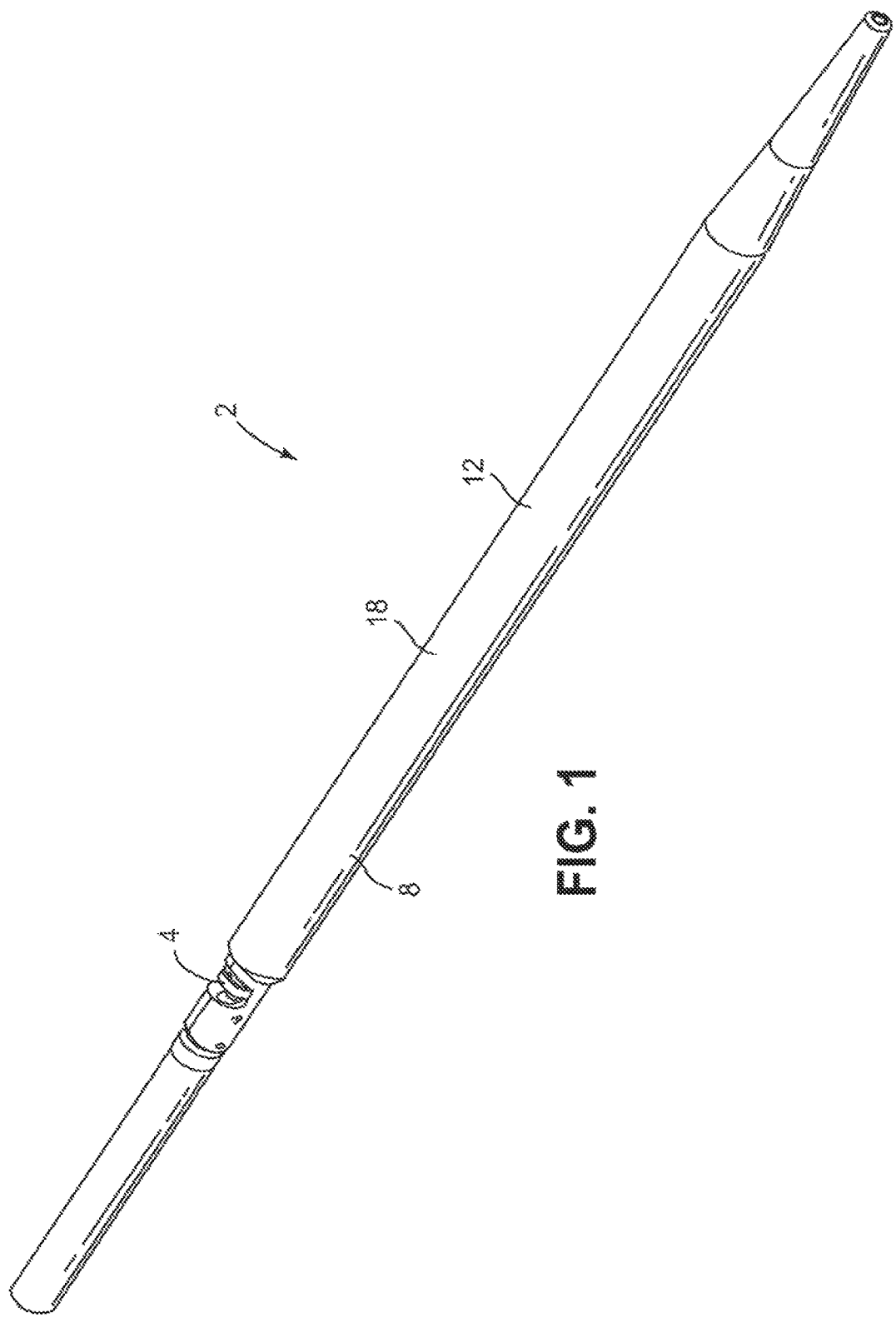
FIG. 1 shows a distal end of an atherectomy catheter.

Referring to FIGS. 1-4, an atherectomy catheter 2 is shown which has a cutting element 4, which is used to cut material from a blood flow lumen. The cutting element 4 is movable between a stored position (FIG. 2) and a cutting position (FIG. 3) relative to an opening 6 in a body 8 of the catheter 2. The cutting element 8 moves outwardly relative to the opening 6 so that a portion of the element 4 extends outwardly from the body 8 through the opening 6. The cutting element 4 may be positioned relative to the body 8 and opening 6 so that less than 90 degrees of the cutting element 4 is exposed to cut tissue. Of course, more of the cutting element 4 may he exposed without departing from numerous aspects of the invention.

The catheter 2 is moved distally through a vessel with the cutting element 4 in the working or cutting position as described in further detail below. As the catheter 2 moves through the blood vessel, the tissue is cut by the cutting element 4 and is directed into a tissue chamber 12 positioned distal to the cutting element 4. The tissue chamber 12 may be somewhat elongate to accommodate the tissue, which has been cut.

The cutting element 4 is moved proximally from the stored position so that a cam surface 14 on the cutting element 4 engages a ramp 16 on the body 8 of the catheter 2. The interaction between the cam surface 14 and the ramp 16 causes the cutting element 4 to move to the cutting position and also causes a tip 18 to deflect which tends to move the cutting element 4 toward the tissue to be cut.

The cutting element 4 is coupled to a shaft 20 that extends through a lumen 21 in the catheter 2. The cutting element 4 is rotated about a longitudinal axis LA when the shaft rotates. The cutting element 4 is rotated about 1 to 160,000 rpm but may be rotated at any other suitable speed depending upon the particular application.

Figure 2:
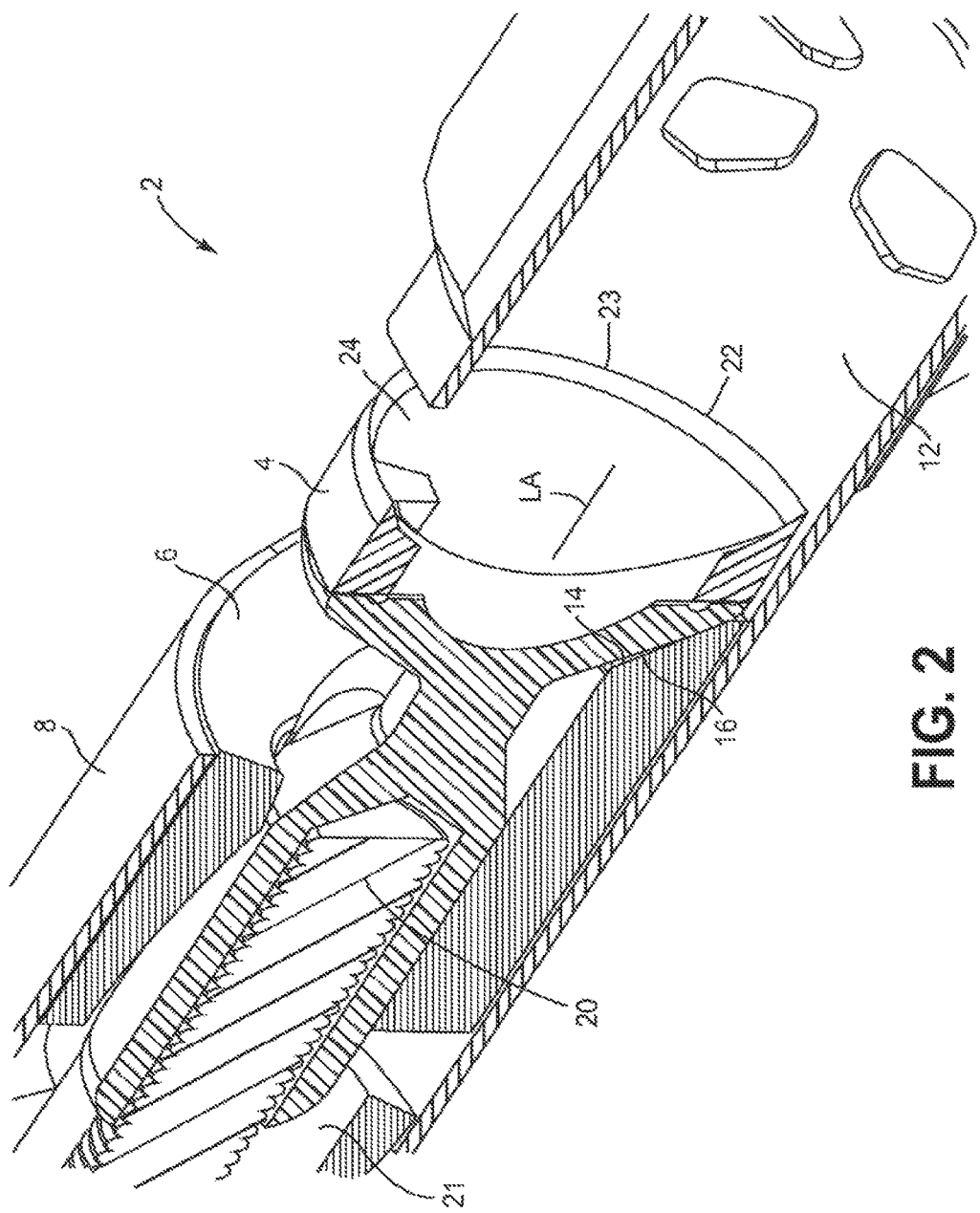
FIG. 2 is a cross-sectional view of the atherectomy catheter with a cutting element in as stored position.
Figure 3:
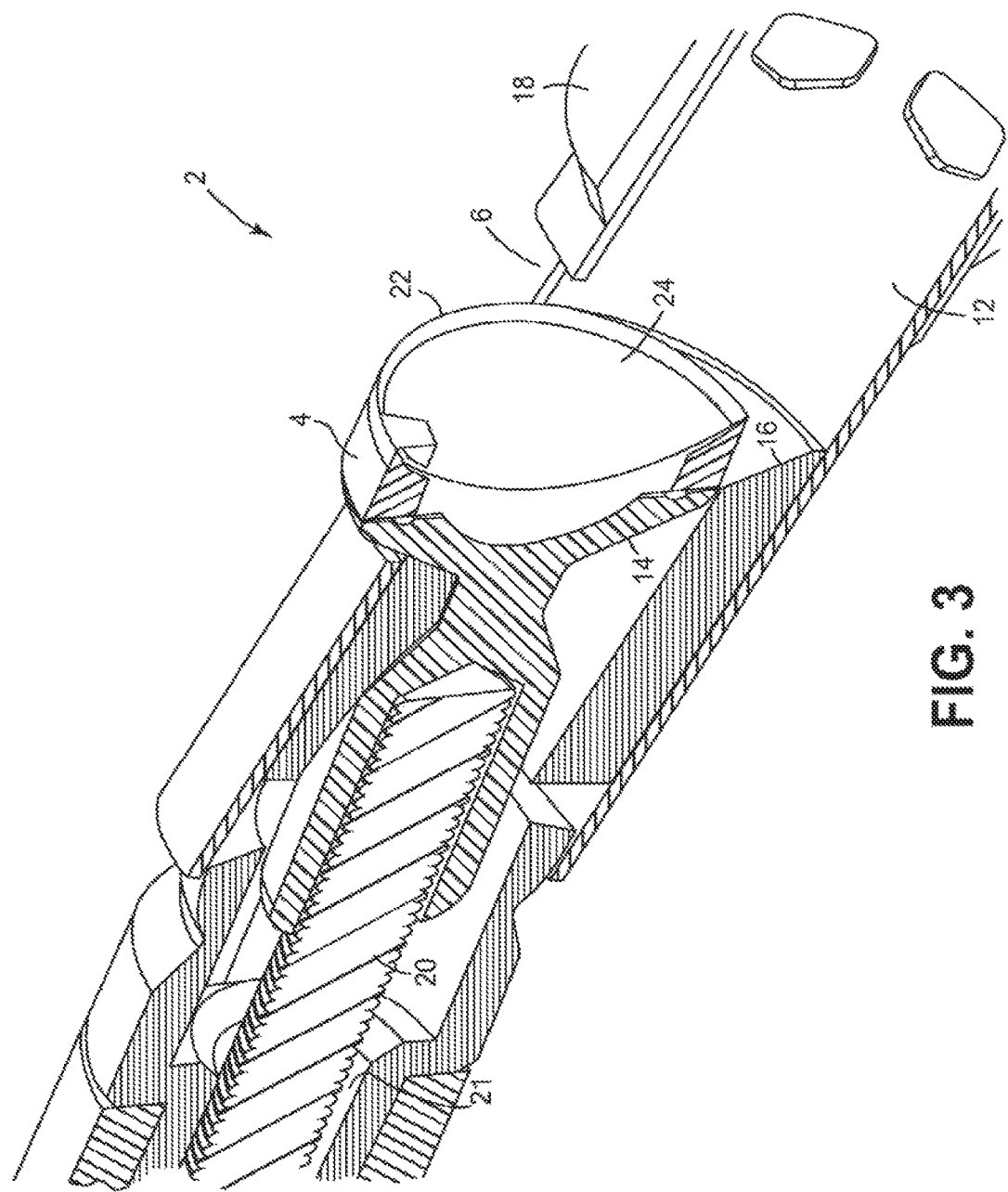
FIG. 3 is a cross-sectional view with a cutting element in a working position.
Figure 4:
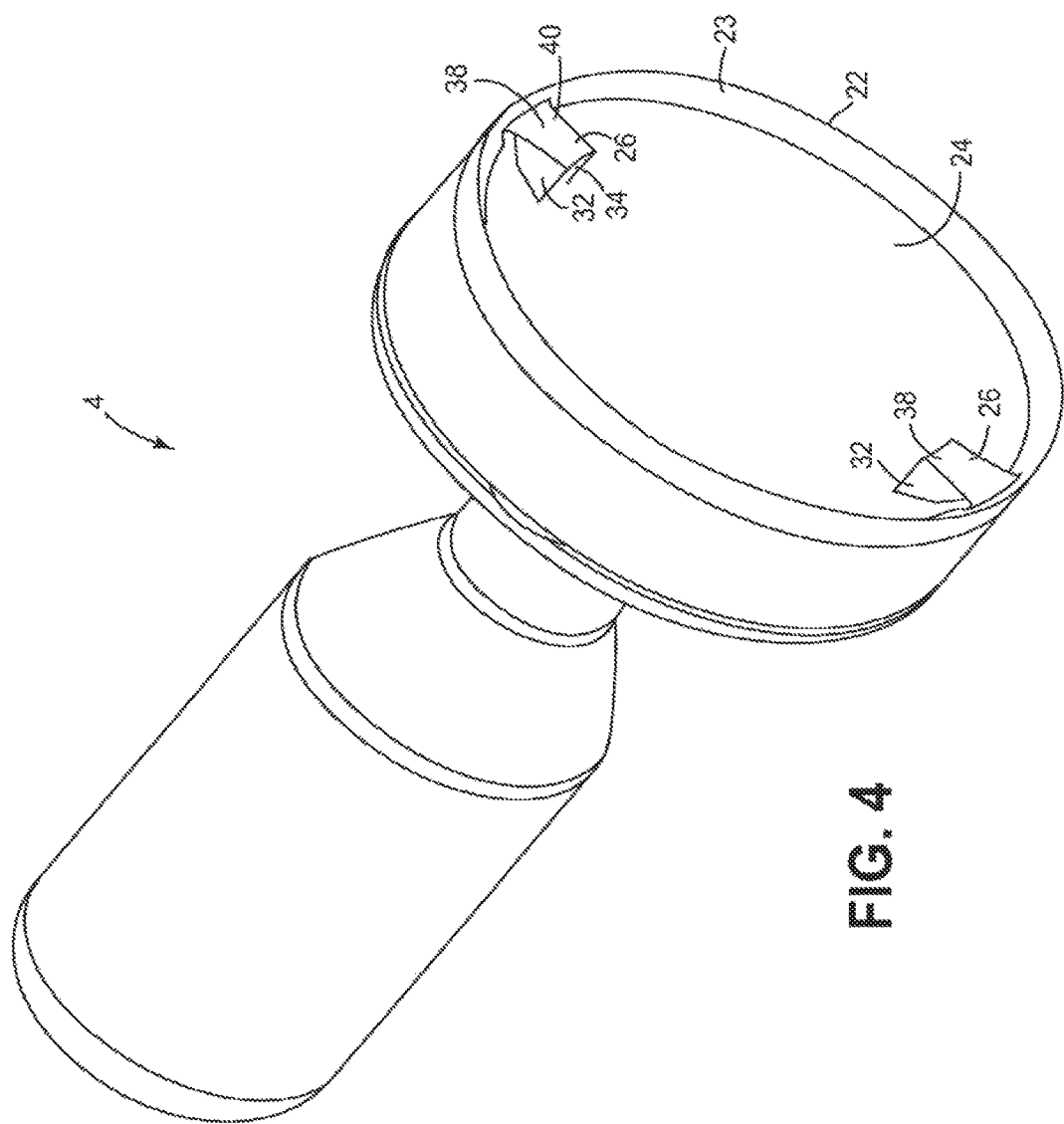
FIG. 4 shows an embodiment of a cutting element.
Figure 5:
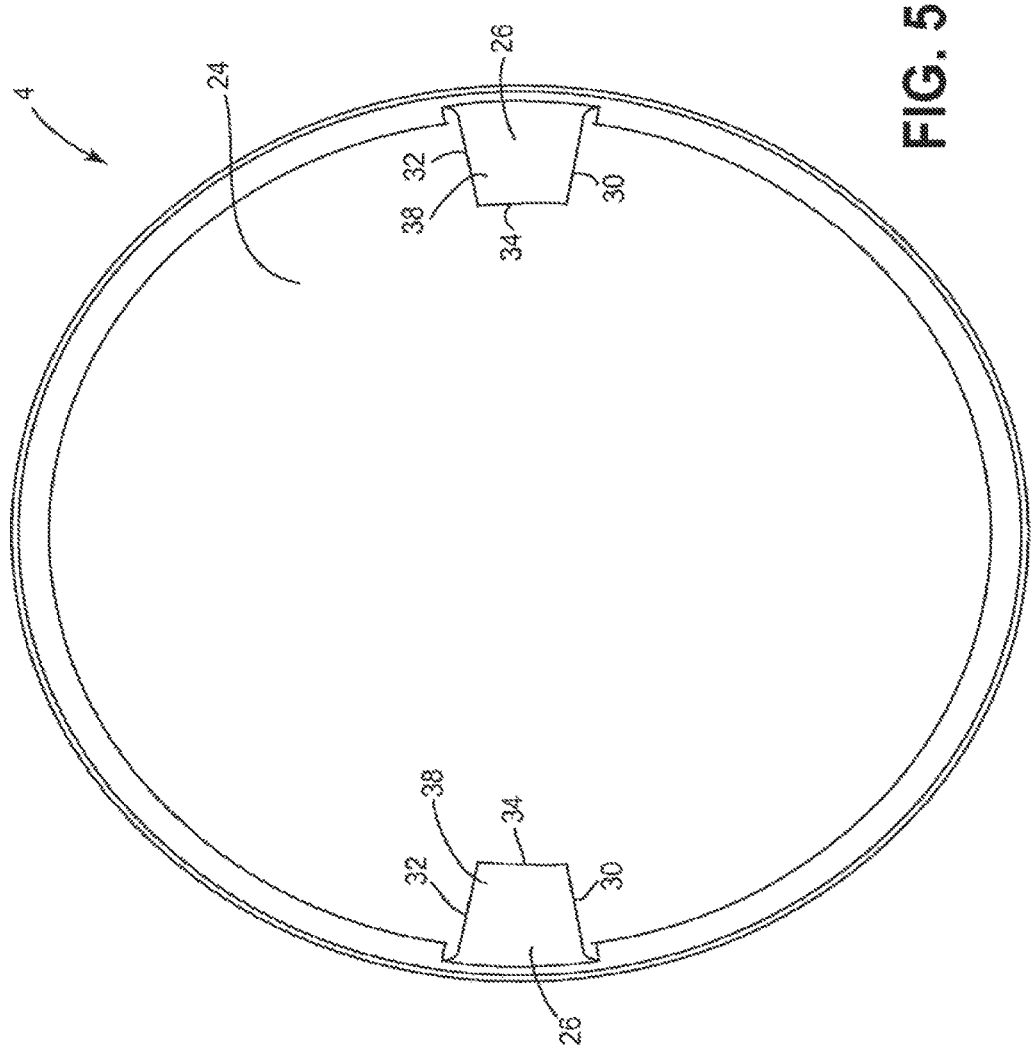
FIG. 5 shows an end view of an embodiment of a cutting element.

Referring to FIGS. 2, 4 and 5, the cutting element 4 is shown when viewed along the longitudinal axis LA. The term "along the longitudinal axis" as used herein shall mean the view of FIG. 5 that shows the distal end of the cutting element 4 when viewed in the direction of the longitudinal axis and/or the axis of rotation. The cutting element 4 has a cutting edge 22 that may be a continuous, uninterrupted, circular-shaped edge although it may also include ridges, teeth, serrations or other features without departing from the scope of the invention. The cutting edge 22 may be at a radially outer edge 23 of the cutting element 4 when the cutting element 4 is in the cutting position.

The cutting element 4 has a cup-shaped surface 24, which directs the tissue cut by the cutting edge 22 into the tissue chamber 12. The cup-shaped surface 24 may be a smooth and continuous surface free of throughholes, teeth, fins or other features, which disrupt the smooth nature of the surface 24 for at least half the distance from the longitudinal axis LA to the outer radius at the cutting edge 22. The cup-shaped surface 24 may also be free of any such features throughout an area of at least 300 degrees relative to the longitudinal axis LA.

Figure 6:
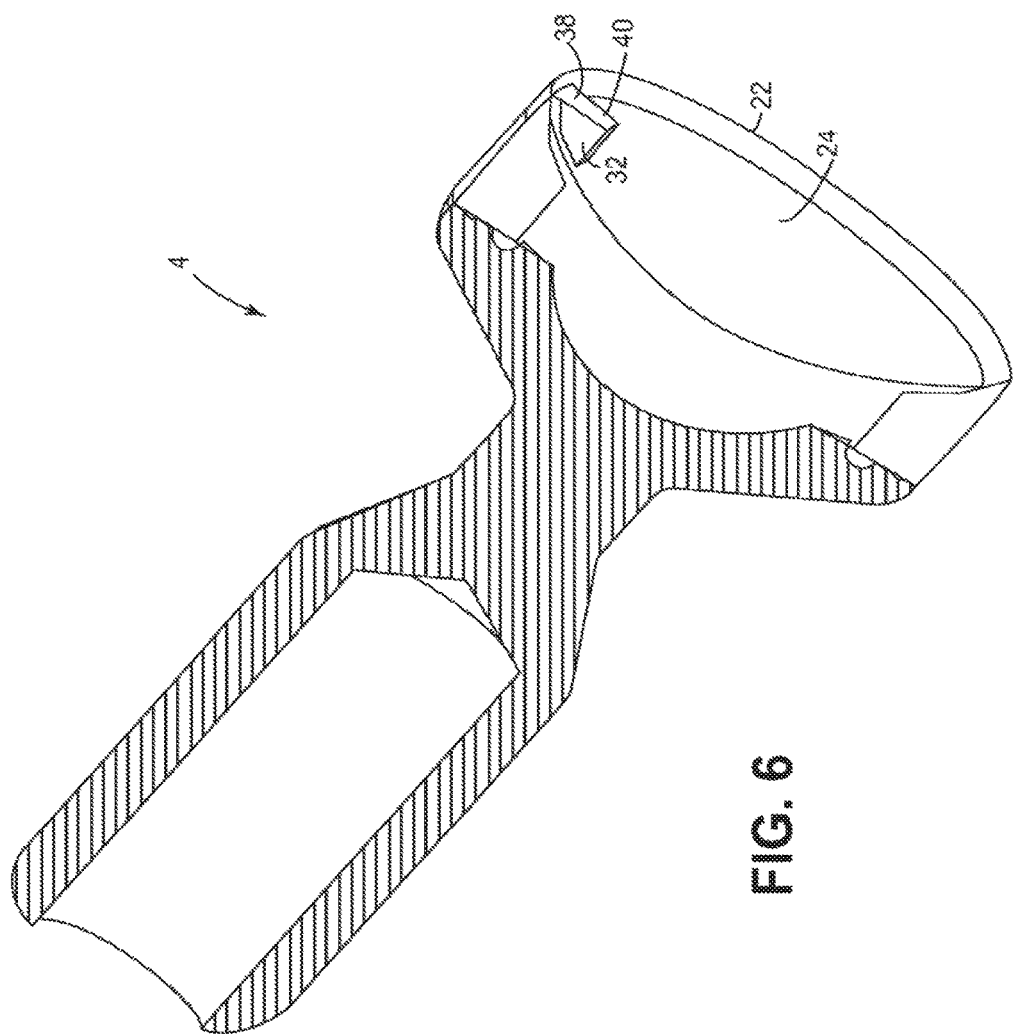
FIG. 6 is a cross-sectional view of an embodiment of a cutting element.

Referring to FIG. 4-6, one or more raised elements 26 extend outwardly from the cup-shaped surface 24 with FIG. 5 showing two raised elements 26. The raised element 26 is a small wedge of material that rises relatively abruptly from the cup-shaped surface 24. The raised element 26 has a first wall 30 and a second wall 32 that both extend radially and form an angle of about 20 degrees therebetween so that the two raised elements 26 together occupy an area of about 40 degrees and altogether may be less than 60 degrees. A third wall 34 extends between the radially inner portion of the first and second walls 30, 32. The raised element 26 helps to break up hard tissue and plaque by applying a relatively blunt force to the hard tissue or plaque since cutting such tissue with the cutting edge 22 is often not effective.

The raised elements 26 altogether occupy a relative small part of the cup-shaped surface 24. The raised elements 26 together may occupy less than 5% of as surface area of the cutting element 4. The term "surface area of the cutting element" as used herein shall mean the surface area which is radially inward from the outer or cutting edge 22 and is exposed when viewed along the longitudinal axis LA. Stated another way, at least 95% of the surface area of the cutting element is a smooth cup-shaped surfaced when viewed along the longitudinal axis. By sizing and positioning the raised element 26 in this manner, the raised element 26 does not interfere with the ability of the cutting element 4 to cut and re-direct tissue into the tissue chamber while still providing the ability to break up hard tissue and plaque with the raised element 26.

The raised element 26 may be recessed from the cutting edge 22 longitudinally and/or radially. The raised element 26 may be recessed longitudinally from the cutting edge 0.0010 to 0.0020 inch and may be about 0.0015 inch. The raised element 26 may be recessed radially from the cutting edge 22 by about the same amount. A distal wall 38 of the cutting element 4 forms a flat surface 40, which is perpendicular to the longitudinal axis LA so that the entire surface is recessed the same distance from the cutting edge. The distal wall 38 may take any other shape, such as a curved shape, or may be tilted, inclined or beveled as now described.

Figure 7:
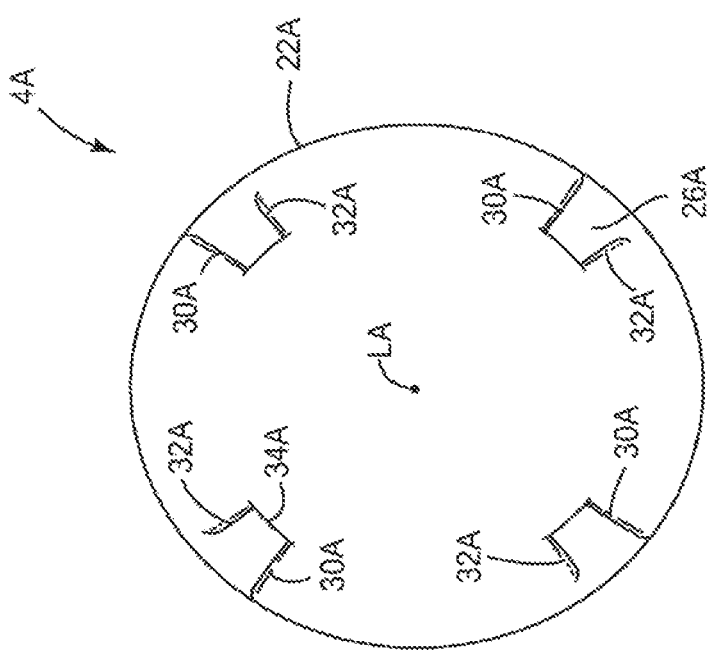
FIG. 7 shows another embodiment of a cutting element which may be used with the atherectomy catheter.

Referring to FIGS. 7, 8 and 8A, another cutting element 4A is shown wherein the same or similar reference numbers refer to the same or similar structure and all discussion concerning the same or similar features of the cutting element 4 are equally applicable here. The cutting element 4A has a cutting edge 22A that may be a continuous, uninterrupted, circular-shaped edge although it may also include ridges, teeth, serrations or other features without departing from the scope of the invention. The cutting edge 22A may he at a radially outer edge 23A of the cutting element 4A when the cutting element 4A is in the cutting position. The cutting element 4A has a cup-shaped surface 24A that directs the tissue cut by the cutting edge 22A into the tissue chamber 12 (see FIG. 2). The cup-shaped surface 24A may be a substantially smooth arid continuous surface as described shove in connection with the cutting element 4.

One or more raised elements 26A, extend outwardly from the cup-shaped surface 24A. FIG. 8 shows four raised elements 26A but may include any number such as 2, 3, 4, 6 or 8 raised elements. The raised clement 26A is a small wedge of material that rises relatively abruptly from the cup-shaped surface 24A. The raised element 26A has a first wall 30A and a second wall 32A which both extend radially and form an angle of about 1 to 30 degrees therebetween so that the four raised elements 26A together occupy an area of about 4 to 60 degrees and altogether may be less than 60 degrees altogether. A third wall 34A extends between the radially inner portion of the first and second walls 30A, 32A. The raised elements 26A may occupy a relative small part of the cup-shaped surface 24A and may be recessed from the cutting edge 22A in the manner described above in connection with the cutting element 4.

A distal wall 38A of the cutting element 4A has a surface 40A that forms an angle of about 30-90 degrees with respect to the longitudinal axis LA. The entire surface 40A may still be somewhat close to but recessed from the cutting edge 22A so that the entire surface 40A is 0.0010 to 0.0050 inch from the cutting edge. An edge 50 formed at the intersection of wall 30A and distal wall 38A is closer to the cutting edge 22A than an edge 52 formed at the intersection of wall 32A and distal wall 38A. The cutting element 4A may be rotated in either direction so that the raised edge 50 may be the leading or trailing edge. The raised edge may be 0.0010 to 0.0020 inch from the cutting edge. The raised elements 26A may all be formed in the same manner or may be different from one another. For example. some of the elements 26A could be angled in different directions so that two of the elements have the raised edge 50 as the leading edge and two of the elements 26A have the raised edge 50 as the trailing edge. The raised elements 26A may also subtend different angles, be of different heights or may have different radial lengths without departing from various aspects of the present invention.

Use of the catheter 2 is now described in connection with the cutting element 4 but is equally applicable to use of the catheter 2 with the cutting element 4A. The catheter 2 is introduced into the patient in a conventional manner using a guidewire (not shown) or the like. The catheter 2 is advanced with the cutting element in the stored position of FIG. 2 until the catheter is positioned at the location where material is to be removed. The cutting element 4 is then moved proximally so that the ramp 16 and cam surface 14 engage to move the cutting element 4 to the cutting position of FIG. 3 and to deflect the tip of the catheter 2. to move the cutting element 4 toward the tissue, to be cut. The cutting element 4 is rotated about longitudinal axis LA and catheter 2 is then moved distally through the vessel so that the cutting element 4 cuts tissue. The tissue, which has been cut, is directed into the tissue chamber 12.

The present invention has been described in connection with preferred embodiments but may, of course, be practiced while departing from the above described embodiments. For example, three or more raised elements may be provided or cutting edge may be serrated without departing from numerous aspects of the present invention.

What is claimed is:

1. An atherectomy catheter, comprising:

a body having opposite proximal and distal ends;

a rotatable shaft coupled to the body;

a cutting element adjacent the distal end of the body and coupled to the rotatable shaft, such that the rotatable shaft is able to rotate the cutting element through a complete rotation about a longitudinal axis of the cutting element, the cutting element having opposite first and second longitudinal ends, a cutting edge extending circumferentially at the first longitudinal end of the cutting element, and an interior surface recessed longitudinally from the cutting edge; and a raised element extending longitudinally outward from the interior surface of the cutting element toward the first longitudinal end of the cutting element, the raised element having a first side wall extending inward from the interior surface generally toward the longitudinal axis of the cutting element, and a longitudinal end wall defining a longitudinal end surface of the raised element which intersects the first side wall to form a first raised edge of the raised element, wherein the raised element further has a second side wall extending inward from the interior surface generally toward the longitudinal axis of the cutting element, wherein the longitudinal end surface of the raised element intersects the second side wall to form a second raised edge of the raised element.

2. The catheter of claim 1, wherein the longitudinal end surface of the raised element forms an angle from 30 degrees to 90 degrees with respect to the longitudinal axis of the cutting element.

3. The catheter of claim 1, wherein the first raised edge has inner and outer ends relative to the longitudinal axis of the cutting element, wherein the inner end of the first raised edge is spaced radially inward from the cutting edge a distance of 0.0010 in (0.0254 mm) to 0.0020 in (0.0508 mm).

4. The catheter of claim 1, wherein the first raised edge has inner and outer ends relative to the longitudinal axis of the cutting element, wherein the outer end of the first raised edge is recessed longitudinally from the cutting edge.

5. The catheter of claim 4, wherein the first raised edge has inner and outer ends relative to the longitudinal axis of the cutting element, wherein the outer end of the first raised edge is recessed from the cutting edge by a longitudinal distance of 0.0010 in (0.0254 mm) to 0.0020 in (0.0508 mm).

6. The catheter of claim 1, wherein the second raised edge is recessed longitudinally relative to the first raised edge.

7. The catheter of claim 1, wherein the rotatable shaft is configured to rotate the cutting element so that the first raised edge is the leading edge and the second raised edge is the trailing edge.

8. The catheter of claim 1, wherein the raised element further has an inner wall extending between and intersecting the first and second side walls and the longitudinal end wall and the interior surface of the cutting element, respectively.

* * * * *